(12) United States Patent
Gelb et al.

(10) Patent No.: US 8,802,833 B2
(45) Date of Patent: Aug. 12, 2014

(54) METHOD FOR 2-SULFATION OF GLYCOSIDES

(75) Inventors: Michael H. Gelb, Seattle, WA (US); Sophie Blanchard, Seattle, WA (US)

(73) Assignee: University of Washington, Seattle, WA (US)

( * ) Notice: Subject to any disclaimer, the term of this patent is extended or adjusted under 35 U.S.C. 154(b) by 368 days.

(21) Appl. No.: 13/144,048

(22) PCT Filed: Jan. 12, 2010

(86) PCT No.: PCT/US2010/020801
§ 371 (c)(1),
(2), (4) Date: Aug. 11, 2011

(87) PCT Pub. No.: WO2010/081163
PCT Pub. Date: Jul. 15, 2010

(65) Prior Publication Data
US 2011/0288281 A1    Nov. 24, 2011

Related U.S. Application Data

(60) Provisional application No. 61/144,024, filed on Jan. 12, 2009.

(51) Int. Cl.
*C07H 1/00* (2006.01)
*C07H 13/04* (2006.01)
*C07H 17/075* (2006.01)

(52) U.S. Cl.
USPC ........................................................ 536/17.5

(58) Field of Classification Search
USPC ........................................................ 514/17.5
See application file for complete search history.

(56) References Cited

U.S. PATENT DOCUMENTS

| 5,783,693 A | 7/1998 | Bertozzi |
| 5,874,548 A * | 2/1999 | Flitsch et al. ................ 536/1.11 |
| 6,184,196 B1 | 2/2001 | Bazin |

OTHER PUBLICATIONS

Tsuda et al, Chem. Pharm. Bull., 1983, 39(11), 2883-87.*
Davis, B.G., "Recent Developments in Glycoconjugates," Journal of the Chemical Society, Perkin Transactions 1, Issue 22, pp. 3215-3237, 1999.
Gridley, J.J., and H.M.I. Osborn, Recent Advances in the Construction of β-D-Mannose and β-D-Mannosamine Linkages, Journal of the Chemical Society, Perkin Transaction 1, Issue 10, pp. 1471-1491, 2000.
International Search Report and Written Opinion mailed Oct. 6, 2010, in corresponding International Application No. PCT/US2010/020801, filed Jan. 12, 2010, 6 pages.
Abad-Romero, B., et al., "Synthesis of Regioselectively Sulfated Xylodextrins and Crystal Structure of Sodium Methyl β-D-Xylopyranoside 4-O-Sulfate Hemihydrate," Carbohydrate Research 344(1):21-28, Jan. 2009.
Blanchard, S., et al., "Short Synthetic Sequence for 2-Sulfation of α-L-Iduronate Glycosides," Carbohydrate Research 344(8):1032-1033, May 2009.
Extended European Search Report mailed Jun. 14, 2012, issued in corresponding European Application No. EP 10 72 9677.4, filed Jan. 12, 2010, 5 pages.
First Office Action, mailed May 20, 2014, issued in corresponding Japanese Application No. 2011-545532, filed Jan. 12, 2010, 6 pages.

* cited by examiner

*Primary Examiner* — Ganapathy Krishnan
(74) *Attorney, Agent, or Firm* — Christensen O'Connor Johnson Kindness PLLC

(57) ABSTRACT

Method for selective 2-sulfation of glycosides.

18 Claims, 3 Drawing Sheets

METHOD FOR 2-SULFATION OF GLYCOSIDES

STATEMENT OF GOVERNMENT LICENSE RIGHTS

This invention was made with Government support under Contract No. 5R01DK067859-09, awarded by the National Institutes of Health. The Government has certain rights in the invention.

CROSS-REFERENCES TO RELATED APPLICATIONS

This application is the National Stage of International Application No. PCT/US2010/020801, filed Jan. 12, 2010, which claims the benefit of U.S. Provisional Application No. 61/144,024, filed Jan. 12, 2009. Each application is expressly incorporated herein by reference in its entirety.

BACKGROUND OF THE INVENTION

The development of new technology for the newborn screening of Hunter syndrome (mucopolysaccharidosis-II) is warranted because of the development of treatments which are most effective when started early in life. This lysosomal storage disease is caused by deficiency in the enzyme iduronate-2-sulfatase, which is needed for the degradation of dermatan sulfate and heparan sulfate, two components of cellular glycosaminoglycans. The assay of this sulfatase requires the use of α-L-iduronate glycosides containing a sulfate at the 2-position.

Synthetic substrates used to assay iduronate-2-sulfatase in vitro are usually disulfated disaccharides derived from nitrous acid degradation of heparin. Such substrates have been useful for the development of a tandem mass spectrometry assay for the newborn screening of Hunter syndrome. However, more recently it has become apparent that the scale-up synthesis using nitrous acid degradation of heparin is impractical to obtain the amount of material needed to support worldwide newborn screening of Hunter syndrome.

A need exists for a new method for the total synthesis of appropriate substrates that can be used at the tens of grams per year scale.

SUMMARY OF THE INVENTION

The present invention provides a method for sulfating a glycoside at the 2-position. In one embodiment, the method includes treating a glycoside having hydroxyl groups at positions 2 and 4 in a cis relationship with a tin reagent to provide a glycoside 2,4-stannylene acetal, and treating the 2,4-stannylene acetal with a sulfating agent to provide a 2-sulfated glycoside. The method of the invention selectively sulfates the glycoside position 2 in favor of position 4. In one embodiment, the 2-sulfated glycoside is sulfated at the 2-position with a selectivity greater than about 90% (relative to position 4 sulfation). In one embodiment, the 2-sulfated glycoside is sulfated at the 2-position with a selectivity is greater than about 95% (relative to position 4 sulfation).

In one embodiment, the glycoside is an iduronate glycoside. In one embodiment, the glycoside is an α-L-iduronate glycoside.

Tin reagents useful in the method of the invention include tin reagents capable of forming stannylene acetals. Representative tin reagents include dialkyltin (IV) oxides, such as dibutyltin (IV) oxide.

Sulfating agents useful in the method of the invention include sulfur trioxide reagents such as sulfur trioxide complexes with trimethylamine, pyridine complex, and sulfur trioxide N,N-dimethylformamide.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION OF THE INVENTION

Figure 1:
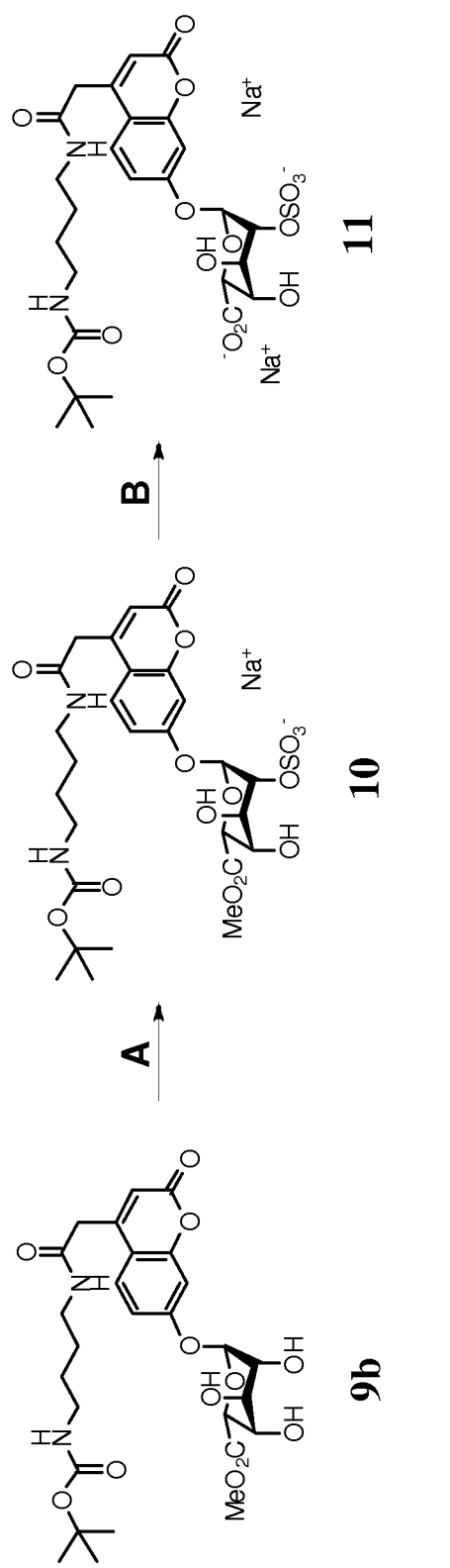
FIG. 1 is a schematic illustration of the selective 2-sulfation of a representative iduronate glycoside in accordance with method of the invention.

The present invention provides a method for sulfating a glycoside at the 2-position. In one embodiment, the method includes treating a glycoside having hydroxyl groups at positions 2 and 4 in a cis relationship with a tin reagent to provide a glycoside 2,4-stannylene acetal, and treating the 2,4-stannylene acetal with a sulfating agent to provide a 2-sulfated glycoside.

As used herein, the term "glycoside" refers to a compound in which a sugar group (glycone) is bonded through its anomeric carbon to another group (aglycone) by a glycosidic bond. Suitable glycosides useful in the method of the invention include sugar groups that are monosaccharides (e.g., pyranoses and furanoses) with hydroxyl groups at positions 2 and 4 of the sugar's ring and having a cis relationship (i.e., the 2- and 4-hydroxyl groups can form a stannylene acetal with the tin reagent). In one embodiment, the glycoside is an O-glycoside (i.e., glycone bonded to aglycone through the glycone anomeric carbon oxygen). The glycosidic bond may have either an a or β configuration. The nature of the glycoside's aglycone is not critical in the method of the invention. Suitable glycones do not interfere with the sulfation of the method. Representative glycones include aromatic compounds (e.g., phenyl- or benzo-containing compounds linked through the aromatic group, for example, coumarins), other carbohydrates, and polycyclic compounds (e.g., steroids).

The method of the invention selectively sulfates the glycoside position 2 in favor of position 4. In one embodiment, the 2-sulfated glycoside is sulfated at the 2-position with a selectivity greater than about 90% (relative to position 4 sulfation). In one embodiment, the 2-sulfated glycoside is sulfated at the 2-position with a selectivity is greater than about 95% (relative to position 4 sulfation).

As noted above, the nature of the glycoside's aglycone can be widely varied. In one embodiment, the glycoside is an iduronate glycoside. In one embodiment, the glycoside is an α-L-iduronate glycoside. Iduronate glycoside sulfates formed by the method of the invention are useful in assays for the enzyme iduronate-2-sulfatase in newborn screening for Hunter syndrome (mucopolysaccharidosis-II).

In one embodiment, the glycoside is an iduronate glycoside having the formula:

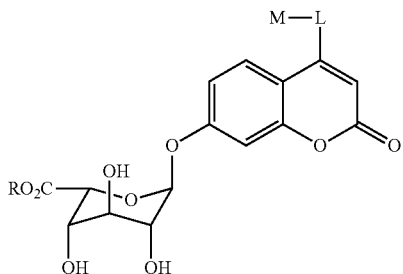

wherein the glycoside forms a parent ion when subjected to electrospray ionization—tandem mass spectrometry, M is a moiety that cleaves from the parent ion to provide a fragment ion on collision-induced dissociation, L covalently links M to the glycoside moiety, and R is a C1-C6 alkyl group. Representative M groups include butyloxycarbonyl (M is $C_4H_9OC(=O)-$). Representative L groups include linkers such as $-NH-(CH_2)_n-NHC(=O)CH_2-$, where n is 1-8. Sulfation of this iduronate glycoside provides a 2-sulfated glycoside having the formula:

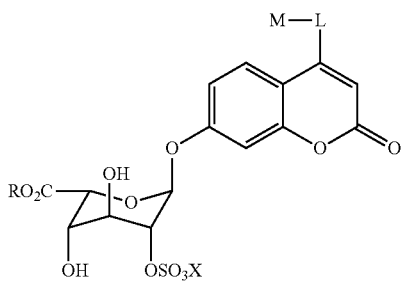

wherein M, L, and R are as above, and X is a hydrogen or a counterion. Representative X groups include ammonium ions such as trimethylammonium ion, and metals ions such as sodium ion. Saponification of this 2-sulfated iduronate glycoside provides an iduronate glycoside having the formula:

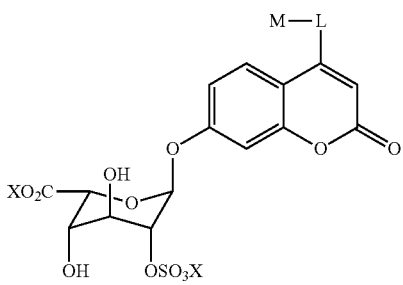

wherein M, L, and X are as above.

In another embodiment, the glycoside is an α-L-iduronate glycoside having the formula:

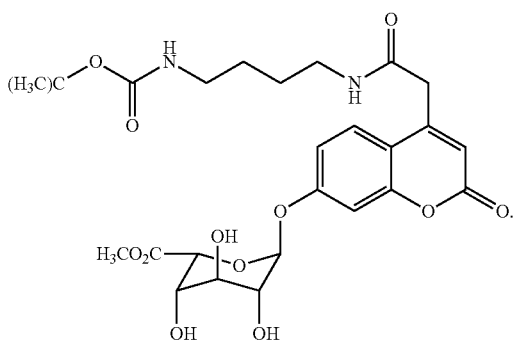

Sulfation of this iduronate glycoside provides a 2-sulfated glycoside having the formula:

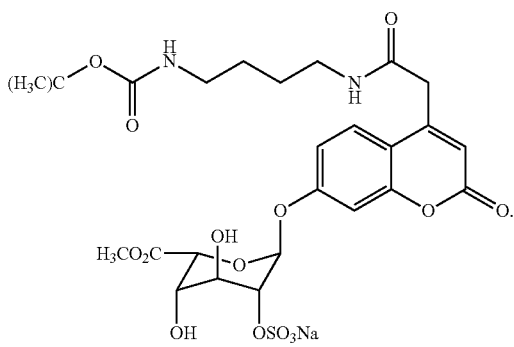

Saponification of this 2-sulfated iduronate glycoside provides an iduronate glycoside having the formula:

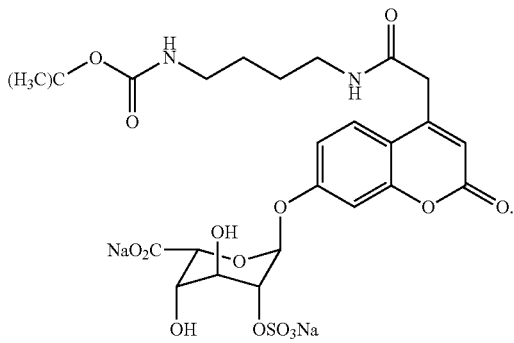

The saponified 2-sulfated iduronate glycoside is useful in assays for the enzyme iduronate-2-sulfatase as described below.

Tin reagents useful in the method of the invention include tin reagents capable of forming stannylene acetals. Representative tin reagents include dialkyltin (IV) oxides, such as dibutyltin (IV) oxide.

Sulfating agents useful in the method of the invention include sulfur trioxide reagents such as sulfur trioxide complexes with trimethylamine, pyridine complex, and sulfur trioxide N,N-dimethylformamide.

As noted above, in one embodiment, the present invention provides a method for selective 2-sulfation of iduronate glycosides. Although there are a number of reports of the synthesis of sulfated saccharide building blocks that have been used to prepare heparin and heparan sulfate fragments, there are no reports on the facile incorporation of sulfate at the 2-position of α-L-iduronate glycosides. In the method of the invention, iduronate glycosides are sulfated at the 2-position with a selectivity greater than 90% compared to sulfation at the 4-position.

The 2-sulfate compound can be used to assay iduronate-2-sulfatase using either a fluorometric assay or via tandem mass spectrometry with electrospray ionization. The fluorometric assay is made possible by the presence of the umbelliferyl moiety. In this case the assay mixture is supplemented with the enzyme α-L-iduronidase, which cleaves the glycosidic linkage to release the fluorescent umbelliferone only after the iduronate-2-sulfatase removes the 2-sulfate group. For the tandem mass spectrometry assay, the α-L-iduronidase coupling enzyme is not needed. In this case, the desulfated α-L-iduronate glycoside is detected directly by tandem mass spectrometry. The presence of the butyloxycarbonyl (BOC) group directs the stability of the parent ion so that the fragmentation proceeds exclusively by cleavage of the carbamate (loss of 100 Da).

In one embodiment, the invention provides a three-step process for the introduction of sulfate at the 2-position starting with an ester of iduronate glycosides (e.g., an α-L-iduronate glycoside). The procedure involves protection of the 2- and 4-hydroxyl groups of the iduronate moiety as the dibutyl stannylene acetal, selective sulfation with sulfur trioxide-trimethylamine, and deprotection of the ester to afford the desired 2-sulfate.

A schematic illustration of the selective 2-sulfation of a representative iduronate glycoside (I.e., α-L-iduronate glycoside) in accordance with method of the invention is described in Example 2 and illustrated in FIG. 1. Referring to FIG. 1, the preparation begins with α-L-iduronate glycoside methyl ester 9b, prepared as described in Example 1 and illustrated schematically in FIG. 2. Treatment of methyl ester 9b with 1.5 equivalents of dibutyltin oxide in anhydrous methanol under reflux protects the 2- and 4-hydroxyl groups as the stannylene acetal. The acetal was used without further purification. The acetal was dissolved in anhydrous N,N-dimethylformamide and treated with 1.5 equivalents of sulfur trioxide-trimethylamine complex for 24 h at 55° C. The crude product was submitted to cation exchange chromatography to convert the trimethylammonium salt of the sulfate to the sodium salt, which was purified by flash chromatography over silica gel to provide the 2-sulfated methyl ester 10. 2-Sulfated methyl ester 10 was solubilized in methanol/water and treated with incremental amounts of aqueous sodium hydroxide to saponify the methyl ester. The crude product was purified by flash chromatography over silica gel to give the 2-sulfated glycoside 11 in 96% purity (61% overall yield from compound 9b). The structure was confirmed by $^1$H-NMR and electrospray ionization mass spectrometry. The selectivity of the sulfation was shown by $^1$H-NMR analysis, which indicated that that 96% of the product is sulfated at the 2-position and 4% at the 4-position.

Because there is no enzyme known capable of hydrolyzing the sulfate at the 4-position, removal of the trace amount of 4-sulfate is not necessary prior to enzyme assay of Hunter syndrome. The method of the invention provides iduronate-2-sulfatase substrate 11 useful in the newborn screening assay for Hunter syndrome.

The following examples are provided for the purpose of illustrating, not limiting, the invention.

EXAMPLES

General Methods

Reactions were carried out in dry solvents in oven-dried glassware under a $N_2$ atmosphere. Thin layer chromatography was carried out on silica plates (silica gel 60, F-254 (0.25 mm)). $^1$H-NMR chemical shifts are reported in parts per million (δ) using the methanol peak as the internal standard (3.31 ppm). Electrospray ionization mass spectra were acquired on an Bruker Esquire LC00066 ion trap spectrometer. Flash chromatography was carried out with silica gel (40-63 μm).

Example 1

The Preparation of α-L-Iduronate Glycoside Methyl Ester

Figure 2:
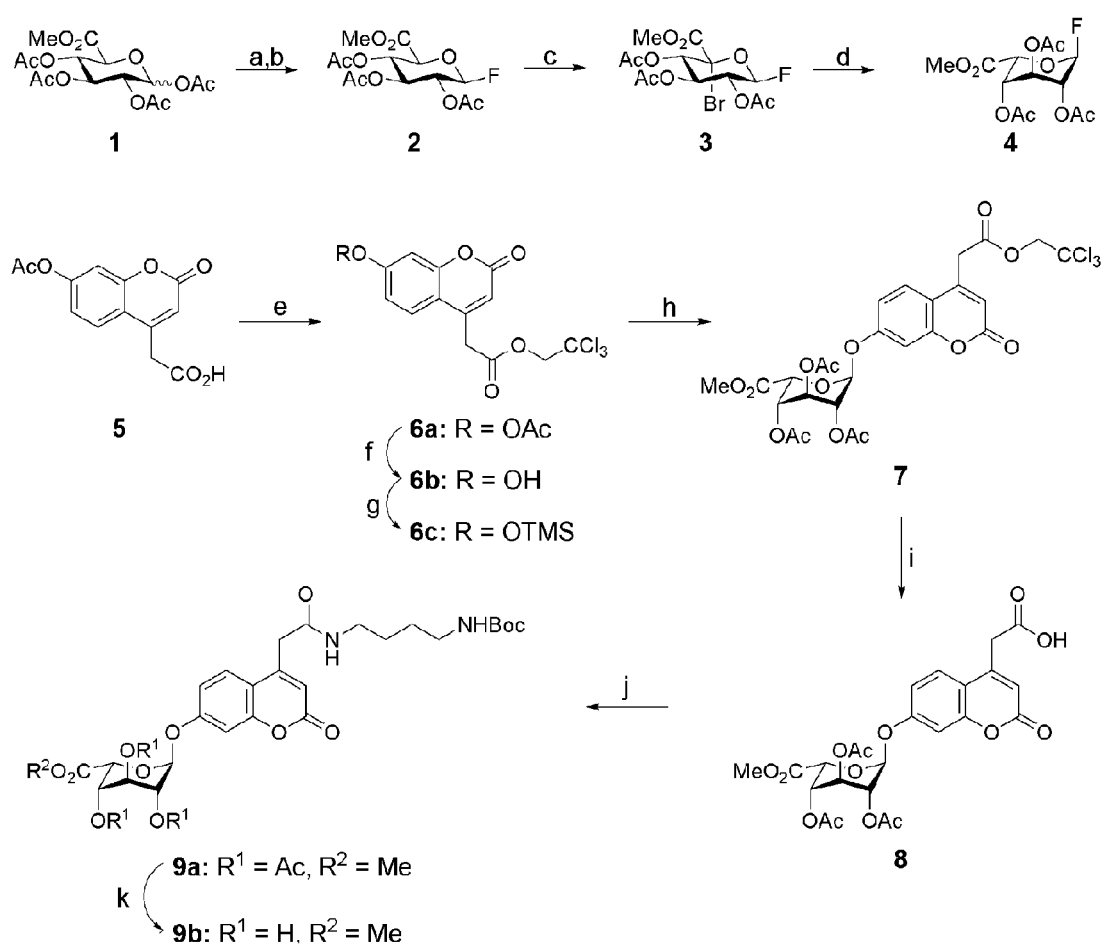
FIG. 2 is a schematic illustration of the synthesis of an iduronate glycoside starting material (α-L-iduronate glycoside methyl ester) useful in the 2-sulfation of a representative iduronate glycoside in accordance with method of the invention.
Figure 3:
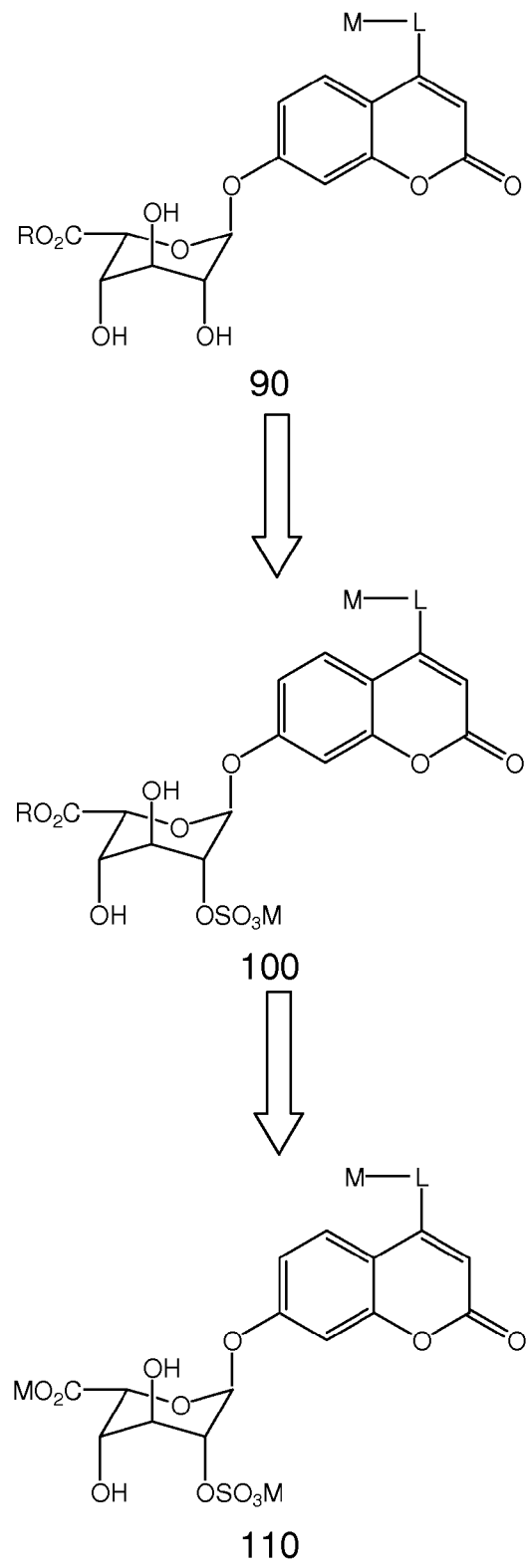
FIG. 3 is a schematic illustration of the selective 2-sulfation of a generalized iduronate glycoside in accordance with method of the invention.

The preparation of α-L-iduronate glycoside methyl ester 9b is described below and illustrated in FIG. 2.

Methyl (2,3,4-tri-O-acetyl-β-D-glucopyranosylfluoride) uronate (2). Methyl 1,2,3,4-tetra-O-acetyl-α, β-D-glucopyranosyluronate 1 (4.98 g, 13.25 mmol, 1 eq) was suspended at 0° C. in 67 mL of 33% hydrobromic acid in acetic acid under nitrogen. After stirring for 15 min at 0° C., the reaction mixture was allowed to warm up to room temperature and stirred for 2 h. The reaction mixture was then diluted with toluene and concentrated under vacuum. The residue was diluted with 250 mL of ethyl acetate and washed with 150 mL of cold saturated sodium bicarbonate and 150 mL of cold brine. The organic layer was dried over $MgSO_4$ and concentrated under vacuum to yield the crude bromide derivative used directly in the next step. The bromide intermediate was dissolved in 167 mL of anhydrous acetonitrile under nitrogen at room temperature. Silver fluoride (3.36 g, 26.49 mmol, 2 eq) was then added. The reaction mixture was stirred for a total of 21 h in the dark. The reaction mixture was filtered through Celite and the filtrate concentrated under vacuum. Column chromatography on silica gel (hexane:EtOAc, 4:1 to 2:1) afforded product 2 (3.3 g, 74%).

Methyl (5-bromo-2,3,4-tri-O-acetyl-(3-D-glucopyranosylfluoride) uronate (3). A suspension of 2 (3.3 g, 9.8 mmol, 1 eq) and N-bromosuccinimide (3.32 g, 18.65 mmol, 1.9 eq) in anhydrous carbon tetrachloride was stirred under nitrogen and under reflux with irradiation for a total of 6 h. N-bromosuccinimide (3.32 g, 18.65 mmol, 1.9 eq) was added after 2 h and 4 h reaction. The reaction mixture was cooled to room temperature and filtered through glass wool. The solvent was removed under vacuum. Column chromatography on silica gel (hexane:EtOAc, 3:1) afforded product 3 (3.12 g, 77%).

Methyl (2,3,4-tri-O-acetyl-α-L-idopyranosylfluoride) uronate (4). Bromide 3 (3.16 g, 7.61 mmol, 1 eq) was dissolved in 50 mL of anhydrous benzene and stirred under nitrogen. Tributyltin hydride (3.1 mL, 11.4 mmol, 1.5 eq) was added, and the reaction mixture was refluxed for 40 min. The mixture was cooled to room temperature, and the solvent was removed under vacuum. Column chromatography on silica gel (toluene:EtOAc, 8:1 to 6:1) afforded product 4 (1.67 g, 65%).

(2',2',2'-Trichloroethyl) 7-acetoxycoumarin-4-acetate (6a). To a suspension of 7-acetoxycoumarin-4-acetic acid 5 (945 mg, 3.6 mmol, 1 eq) in 47 mL of anhydrous dichloromethane at room temperature under nitrogen was added 2,2,2-trichloroethanol (431 μL, 4.5 mmol, 1.25 eq). A solution of N,N'-dicyclohexylcarbodiimide (818 mg, 4 mmol, 1.1 eq) in 10 mL of anhydrous dichloromethane was added. The reaction mixture was stirred for 15 min, after which it was diluted with dichloromethane and filtered. The filtrate was concentrated under vacuum. Column chromatography on silica gel ($CH_2Cl_2$ then $CH_2Cl_2$:EtOAc, 10:1) afforded product 6a (1.37 g, 96%): $R_f$ 0.78 ($CH_2Cl_2$:EtOAc, 5:1); $^1H$ NMR (300 MHz, $CDCl_3$): δ 7.61 (d, 1H, $J_{5,6}$ 8.7 Hz, H-5), 7.15 (d, 1H, $J_{6,8}$ 2.1 Hz, H-8), 7.07 (dd, 1H, $J_{6,8}$ 2.3, $J_{5,6}$ 8.7 Hz, H-6), 6.42 (s, 1H, H-3), 4.77 (s, 2H, $CH_2CCl_3$), 3.91 (2 s, 2H, $CH_2CO_2$), 2.33 (s, 3H, OAc); $^{13}C$ NMR (75 MHz, $CDCl_3$): δ 168.6, 167.0, 154.5, 153.5, 146.5, 125.5, 118.5, 117.0, 116.5, 110.9, 74.6, 37.7, 21.2; ESI-MS: m/z 393 $[M+H]^+$.

(2',2',2'-Trichloroethyl) 7-hydroxycoumarin-4-acetate (6b). A solution of 6a (1.08 g, 2.74 mmol, 1 eq) in 108 mL of anhydrous tetrahydrofuran was prepared under nitrogen at room temperature. A solution of 2 M ammonia in 2-propanol (6.8 mL, 13.7 mmol, 5 eq) was added dropwise. The reaction mixture was stirred at room temperature in a tightly sealed flask for 18 h. The reaction mixture was concentrated under vacuum. Purification by column chromatography on silica gel ($CH_2Cl_2$, then $CH_2Cl_2$:EtOAc, 10:1 to 5:1) afforded product 6b (753 mg, 78%): $R_f$ 0.6 ($CH_2Cl_2$:EtOAc, 5:1); $^1H$ NMR (300 MHz, $d_6$-DMSO): δ 7.55 (d, 1H, $J_{5,6}$ 8.7 Hz, H-5), 6.79 (dd, 1H, $J_{6,8}$ 2.3, $J_{5,6}$ 8.7 Hz, H-6), 6.74 (d, 1H, $J_{6,8}$ 2.3 Hz, H-8), 6.31 (s, 1H, H-3), 4.94 (s, 2H, $CH_2CCl_3$), 4.14 (2 s, 2H, $CH_2CO_2$); $^{13}C$ NMR (75 MHz, $d_6$-DMSO): δ 168.4, 161.8, 160.5, 155.5, 149.2, 127.3, 113.5, 112.9, 111.5, 102.8, 95.5, 74.0, 36.9; ESI-MS: m/z 351 $[M+H]^+$.

(2'',2'',2''-Trichloroethyl) 7-O-(methyl 2',3',4'-tri-O-acetyl-α-L-idopyranosyluronate) coumarin-4-acetate (7). A suspension of 6b (703 mg, 2 mmol, 1.26 eq) and $LiClO_4/SiO_2$ (200 mg) in 2 mL of anhydrous dichloromethane was stirred at room temperature under nitrogen. 1,1,1,3,3,3-Hexamethyldisilazane (835 μL, 4 mmol, 2.52 eq) was added dropwise. The reaction mixture was stirred for 35 min. The reaction mixture was diluted with dichloromethane and filtered. The filtrate was concentrated by rotary evaporation to afford (2',2',2'-trichloroethyl) 7-O-trimethylsilylcoumarin-4-acetate 6c, which was used in the next step without further purification. A solution of glycosyl donor 4 (534 mg, 1.6 mmol, 1 eq) and previously prepared glycosyl acceptor 6c in 10 mL of anhydrous dichloromethane under nitrogen was cooled down to 0° C. Boron trifluoride diethyl etherate (196 μL, 1.6 mmol, 1 eq) was added dropwise, after which the reaction mixture was allowed to warm to room temperature. The reaction flask was tightly sealed, and the reaction mixture was stirred for 1.5 h, and then concentrated under vacuum. The residue was dissolved in acetic anhydride (10 mL), and boron trifluoride diethyl etherate (88 μL) was added. After stirring for 20 min, the reaction was diluted with 200 mL of dichloromethane and washed with 100 mL of water, 100 mL of saturated sodium bicarbonate and 100 mL of brine. The organic layer was dried over $MgSO_4$ and concentrated under vacuum with additional co-evaporations with toluene. Column chromatography on silica gel ($CH_2Cl_2$, then $CH_2Cl_2$:EtOAc, 10:1 to 5:1) afforded product 7 (934 mg, 88%): $[α]_D$ −80° (c 1, $CHCl_3$); $R_f$ 0.5 ($CH_2Cl_2$:EtOAc, 5:1); $^1H$ NMR (300 MHz, $CDCl_3$): δ 7.53 (d, 1H, $J_{5,6}$ 8.7 Hz, H-5), 7.06 (d, 1H, $J_{6,8}$ 2.5 Hz, H-8), 7.01 (dd, 1H, $J_{6,8}$ 2.5, $J_{5,6}$ 8.9 Hz, H-6), 6.33 (s, 1H, H-3), 5.84 (d, 1H, $J_{1',2'}$ 2.5 Hz, H-1'), 5.20 (m, 2H, H-3', H-4'), 5.05 (m, 1H, H-2'), 4.89 (m, 1H, H-5'), 4.77 (2 s, 2H, $CH_2CCl_3$), 3.87 (s, 2H, $CH_2CO_2$), 3.77 (s, 3H, $CO_2Me$), 2.16-2.09 (3 s, 9H, 3 OAc); $^{13}C$ NMR (75 MHz, $CDCl_3$) δ 169.5, 169.4, 169.0, 167.9, 167.2, 160.2, 158.9, 155.3, 146.7, 126.0, 115.7, 114.1, 113.2, 104.9, 95.7, 94.5, 74.6, 67.8, 67.0, 66.8, 52.9, 37.7, 20.9, 20.9, 20.7; ESI-MS: m/z 667 $[M+H]^+$.

(N-[4''-(tert-butoxycarbonylamino)-butyl]) 7-O-(methyl 2',3',4'-tri-O-acetyl-α-L-idopyranosyluronate) coumarin-4-acetamide (9a). Glycoside 7 (831 mg, 1.2 mmol, 1 eq) was dissolved in 41 mL of anhydrous tetrahydrofuran at room temperature. The solution was cooled to 0° C., and 90% aqueous acetic acid (5.5 mL) was added. Finally, copper chloride (167 mg, 1.2 mmol, 1 eq) and zinc dust (813 mg, 12.4 mmol, 10 eq) were added. The reaction mixture was stirred at 0° C. for a total of 39 h, during which zinc dust (813 mg, 12.4 mmol, 10 eq) was added after 15 h and 25 h reaction. The reaction mixture was filtered through Celite, and the filtrate was concentrated under vacuum. The residue was solubilized in 200 mL of dichloromethane and washed with 150 mL of water (twice) and 150 mL brine. The organic layer was dried over $MgSO_4$ and concentrated under vacuum. Column chromatography on silica gel ($CH_2Cl_2$, then $CH_2Cl_2$:EtOAc, 5:1 to 2:1; all solvents with 1% acetic acid) afforded product 8 (634 mg, 95%). A solution of acid 8 (627 mg, 1.2 mmol, 1 eq) in 20 mL of anhydrous tetrahydrofuran was cooled to 0° C. N-(3-Dimethylaminopropyl)-N'-ethylcarbodiimide hydrochloride (245 mg, 1.28 mmol, 1.1 eq) and 1-hydroxybenzotriazole (196 mg, 1.28 mmol, 1.1 eq) were added, and the suspension was stirred for 30 min at 0° C. A solution of N-Boc-1,4-diaminobutane (223 μL, 1.2 mmol, 1 eq) in 2 mL of anhydrous N,N-dimethylformamide was slowly added to the suspension. The reaction mixture was allowed to warm to room temperature and stirred for 3 h. The reaction mixture was concentrated under vacuum. The residue was taken up in 250 mL of ethyl acetate and washed with 150 mL of 1 M HCl, 150 mL of water and 150 mL of brine. The organic layer was dried over $MgSO_4$ and concentrated under vacuum. Column chromatography on silica gel (toluene:acetone, 3:1 to 2:1) afforded product 9a (528 mg, 65%):$[α]_D$ −70° (c 0.85, $CHCl_3$); $R_f$ 0.38 ($CH_2Cl_2$:MeOH, 95:5); $^1H$ NMR (300 MHz, $CDCl_3$): δ 7.67 (d, 1H, $J_{5,6}$ 8.7 Hz, H-5), 7.03 (d, 1H, $J_{6,8}$ 2.3 Hz, H-8), 6.99 (dd, 1H, $J_{6,8}$ 2.5, $J_{5,6}$ 8.7 Hz, H-6), 6.29 (s, 1H, H-3), 5.84 (d, 1H, $J_{1',2'}$ 2.1 Hz, H-1'), 5.20 (m, 2H, H-3', H-4'), 5.04 (m, 1H, H-2'), 4.89 (d, 1H, $J_{4',5'}$ 2.1 Hz, H-5'), 3.77 (s, 3H, $CO_2Me$), 3.65 (s, 2H, $CH_2CONH$), 3.26 (m, 2H, $CH_2NHCO$), 3.09 (m, 2H, $CH_2NHCO$), 2.17-2.09 (3 s, 9H, 3 OAc), 1.49 (m, 4H, $CH_2$—$CH_2$), 1.42 (s, 9H, $CMe_3$); $^{13}C$ NMR (75 MHz, $CDCl_3$) δ 169.4, 169.4, 169.0, 167.8, 167.6, 160.7, 158.8, 156.4, 155.2, 149.7, 126.7, 114.5, 114.5, 113.2, 104.5, 95.6, 79.4, 67.7, 66.9, 66.6, 52.8, 39.8, 28.5, 20.8, 20.8, 20.6; ESI-MS: m/z 707 $[M+H]^+$.

(N-[4''-(tert-butoxycarbonylamino)-butyl]) 7-O-(α-L-idopyranosyluronic acid) coumarin-4-acetamide (9b). A solution of 9a (98 mg, 0.165 mmol, 1 eq) in 16 mL of methanol was cooled to 0° C. A solution of 0.5 M sodium methoxide in methanol (140 μL, 0.07 mmol, 0.4 eq) was added dropwise. The reaction mixture was stirred at 0° C. for 1.5 h. The reaction mixture was neutralized with Amberlite IR-120 ($H^+$) and filtered. The filtrate was concentrated under vacuum. Column chromatography on silica gel ($CH_2Cl_2$ then $CH_2Cl_2$:MeOH, 9:1) afforded product 9b (69 mg, 86%): $^1H$ NMR (300 MHz, $CD_3OD$): δ 7.69 (d, 1H, $J_{5,6}$ 9.7 Hz, H-5), 7.14 (d, 1H, $J_{6,8}$ 2.3 Hz, H-8), 7.13 (dd, 1H, H-6), 6.28 (s, 1H, H-3), 5.76 (d, 1H, $J_{1',2'}$ 3.9 Hz, H-1'), 4.75 (d, 1H, $J_{4',5'}$ 3.5 Hz, H-5'), 3.97-3.89 (m, 2H, H-2', H-3'), 3.77 (s, 3H, $CO_2Me$), 3.74 (s, 2H, $CH_2CONH$), 3.73 (m, 1H, H-4'), 3.21 (m, 2H, $CH_2NHCO$), 3.03 (m, 2H, $CH_2NHCO$), 1.49 (m, 4H, $CH_2$—$CH_2$), 1.42 (s, 9H, $CMe_3$); ESI-MS: m/z 581 $[M+H]^+$.

Example 2

The Preparation of 2-Sulfated α-L-Iduronate Glycoside 11

The preparation of 2-sulfated α-L-iduronate glycoside 11 is described below and is illustrated in FIG. 1.

Synthesis of α-L-Iduronate Glycoside Methyl Ester 10.
Starting material 9b (164.5 mg, 0.28 mmol, 1 eq), prepared as described in Example 1, was solubilized in 16 mL anhydrous methanol, and dibutyltin (IV) oxide (106 mg, 0.42 mmol, 1.5 eq, Aldrich) was added. The reaction mixture was heated under reflux for 40 minutes, after which dibutyltin oxide was completely dissolved. The reaction mixture was allowed to cool and was concentrated under vacuum. The residue was co-evaporated once with toluene to remove traces of water.

The residue was solubilized in 16 mL anhydrous N,N-dimethylformamide. Sulfur trioxide-trimethylamine complex (59.1 mg, 0.42 mmol, 1.5 eq, Aldrich) was added, and the reaction mixture was heated at 55° C. for 24 hours. The reaction mixture was allowed to cool and then quenched with methanol, before being concentrated under vacuum. To convert the product from the trimethylammonium salt to the sodium salt, the residue was submitted to cation-exchange chromatography [Dowex 50WX8-400 (Na$^+$), 1×4 cm] using methanol as the eluent. The sodium salt was purified by column chromatography on silica using methanol/chloroform/water (5/8/1) to give α-L-iduronate glycoside methyl ester 10. TLC (silica, methanol/chloroform/water, 5/8/1): $R_f$=0.6. $^1$H-NMR (300 MHz, CD$_3$OD): 1.43 (s, 9H, t-butyl); 1.50 (m, 4H, CH$_2$CH$_2$); 3.04 (m, 2H, CH$_2$N); 3.21 (t, 2H, CH$_2$N); 3.74 (brs, 2H, CH$_2$CO); 3.76 (s, 3H, CO$_2$Me); 3.99 (brt, 1H, H-4); 4.19 (brt, 1H, H-3); 4.50 (m, 1H,H-2); 4.81 (d, 1H, H-5); 6.00 (brs, 1H, H-1); 6.28 (s, 1H, coumarin vinyl CH); 7.16-7.19 (m, 2H, coumarin CH); 7.70 (d, 1H, coumarin CH).

Synthesis of 2-Sulfated α-L-Iduronate Glycoside 11.

Compound 10 was solubilized in 15.4 mL of methanol/water (1/1) at room temperature. An aqueous solution of sodium hydroxide 0.1 M was added in increments of 0.1 eq of NaOH (283 μL, 0.03 mmol) until the pH of the solution reached approximately 8 (pH paper). The pH was maintained by incremental additions of the 0.1 M NaOH solution as the reaction proceeded (every 15-30 minutes). The reaction mixture was stirred for 5.5 h (1.3 eq NaOH added), after which it was concentrated under vacuum to remove methanol and finally lyophilized overnight. The residue was purified by column chromatography on silica using methanol/chloroform/water (5/8/1) to give 2-sulfated α-L-iduronate glycoside 11 (96% 2-sulfated, 4% 4-sulfated) with 61% overall yield from compound 9b. TLC (silica, methanol/chloroform/water, 5/8/1): $R_f$=0.2. $^1$H-NMR (300 MHz, CD$_3$OD): 1.43 (s, 9H, t-butyl); 1.50 (m, 4H, CH$_2$CH$_2$); 3.04 (t, 2H, CH$_2$N); 3.21 (t, 2H, CH$_2$N); 4.07 (brs, 1H, H-4); 4.17 (brs, 1H, H-3); 4.48 (brs, 1H, H-2); H-5 under water peak; 6.14 (brs, 01H, H-1); 6.17 (s, 1H, coumarin vinyl CH); 7.07-7.12 (m, 2H, coumarin CH); 7.53 (d, 1H, coumarin CH). Electrospray ionization mass spectrometry: (negative mode) (M−H)$^{-1}$, calculated 645.2, observed 645.3.

While illustrative embodiments have been illustrated and described, it will be appreciated that various changes can be made therein without departing from the spirit and scope of the invention.

The embodiments of the invention in which an exclusive property or privilege is claimed are defined as follows:

1. A method for sulfating an iduronate glycoside at the 2-position, comprising:
   (a) treating an iduronate glycoside having hydroxyl groups at positions 2 and 4 in a cis relationship with a tin reagent to provide a glycoside 2,4-stannylene acetal; and
   (b) treating the 2,4-stannylene acetal with a sulfating agent to selectively provide a 2-sulfated iduronate glycoside.

2. The method of claim 1, wherein the 2-sulfated glycoside is sulfated at the 2-position with a selectivity greater than 90%.

3. The method of claim 1, wherein the 2-sulfated glycoside is sulfated at the 2-position with a selectivity greater than 95%.

4. The method of claim 1, wherein the glycoside is an α-L-iduronate glycoside.

5. The method of claim 1, wherein the tin reagent is a dialkyltin IV oxide.

6. The method of claim 1, wherein the tin reagent is dibutyltin (IV) oxide.

7. The method of claim 1, wherein the sulfating agent is sulfur trioxide.

8. The method of claim 1, wherein the sulfating agent is a sulfur trioxide complex selected from the group consisting of sulfur trioxide trimethylamine complex, sulfur trioxide pyridine complex, and sulfur trioxide N,N-dimethylformamide complex.

9. The method of claim 1, wherein the glycoside has the formula:

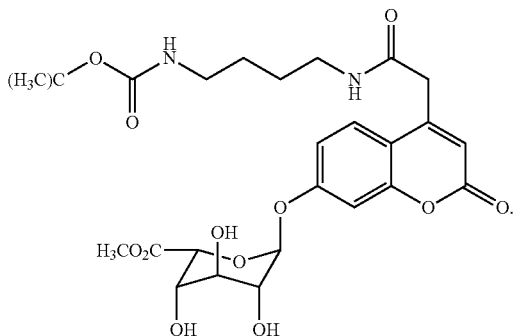

10. The method of claim 1, wherein the 2-sulfated iduronate glycoside has the formula:

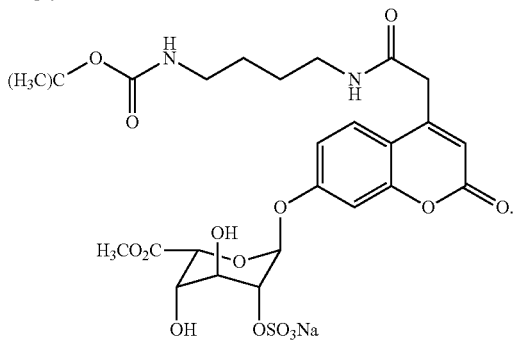

11. The method of claim 10 further comprising saponifying the 2-sulfated glycoside methyl ester to provide a 2-sulfated iduronate glycoside having the formula:

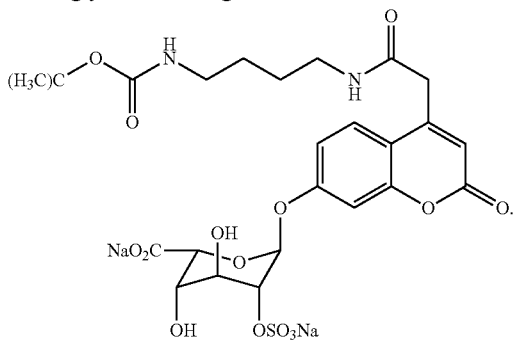

12. The method of claim 1, wherein the iduronate glycoside has the formula:

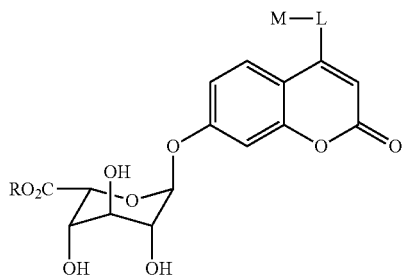

wherein the glycoside forms a parent ion when subjected to electrospray ionization-tandem mass spectrometry, M is a moiety that cleaves from the parent ion to provide a fragment ion on collision-induced dissociation, L covalently links M to the iduronate glycoside moiety, and R is a C1-C6 alkyl group.

13. The method of claim 1, wherein the 2-sulfated iduronate glycoside has the formula:

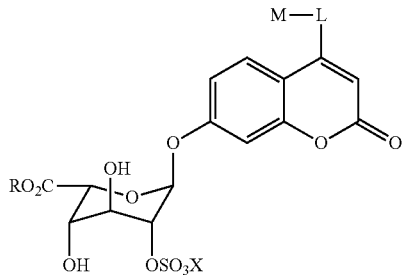

wherein the sulfated iduronate glycoside forms a parent ion when subjected to electrospray ionization-tandem mass spectrometry, M is a moiety that cleaves from the parent ion to provide a fragment ion on collision-induced dissociation, L covalently links M to the iduronate glycoside moiety, R is a C1-C6 alkyl group, and X is hydrogen, an ammonium ion, or a metal ion.

14. The method of claim 13 further comprising saponifying the 2-sulfated glycoside ester to provide a 2-sulfated iduronate glycoside having the formula:

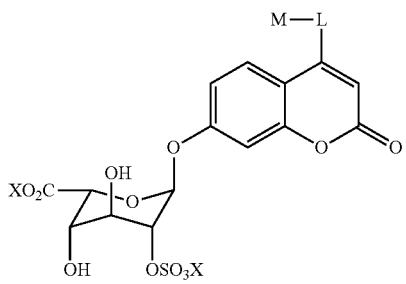

wherein the sulfated iduronate glycoside forms a parent ion when subjected to electrospray ionization-tandem mass spectrometry, M is a moiety that cleaves from the parent ion to provide a fragment ion on collision-induced dissociation, L covalently links M to the iduronate glycoside moiety, and X is hydrogen, an ammonium ion, or a metal ion.

15. The method of claim 13, wherein M is a butyloxycarbonyl [$C_4H_9C(=O)-$].

16. The method of claim 13, wherein L is $-NH-(CH_2)_n-NHC(=O)CH_2-$, where n is 1-8.

17. The method of claim 13, wherein the ammonium ion is trimethylammonium.

18. The method of claim 13, wherein the metal ion is a sodium ion.

* * * * *